US010765459B2

(12) United States Patent
Fiechter et al.

(10) Patent No.: US 10,765,459 B2
(45) Date of Patent: Sep. 8, 2020

(54) OCCIPITAL PLATE FOR OCCIPITO-CERVICAL FIXATION AND SYSTEM FOR OCCIPITO-CERVICAL FIXATION

(71) Applicant: MEDACTA INTERNATIONAL S.A., Castel San Pietro (CH)

(72) Inventors: Meinrad Fiechter, Lugano (CH); Francesco Siccardi, Castel San Pietro (CH); Michele Incandela, Como (IT); Massimiliano Martis, Cassina Rizzardi (IT)

(73) Assignee: Medacta International S.A., Castel San Pietro (CH)

( * ) Notice: Subject to any disclaimer, the term of this patent is extended or adjusted under 35 U.S.C. 154(b) by 27 days.

(21) Appl. No.: 15/777,664

(22) PCT Filed: Nov. 10, 2016

(86) PCT No.: PCT/IB2016/056769
§ 371 (c)(1),
(2) Date: May 19, 2018

(87) PCT Pub. No.: WO2017/085599
PCT Pub. Date: May 26, 2017

(65) Prior Publication Data
US 2018/0344361 A1    Dec. 6, 2018

(30) Foreign Application Priority Data

Nov. 20, 2015    (IT) .................... 102015000074797

(51) Int. Cl.
*A61B 17/70*  (2006.01)
*A61B 17/80*  (2006.01)

(52) U.S. Cl.
CPC ........ *A61B 17/7055* (2013.01); *A61B 17/809* (2013.01); *A61B 17/7001* (2013.01)

(58) Field of Classification Search
CPC .. A61B 17/7055; A61B 17/7058–7059; A61B 17/70; A61B 17/80–8023
See application file for complete search history.

(56) References Cited

U.S. PATENT DOCUMENTS 5,507,746 A * 4/1996 Lin .................... A61B 17/7041
                                                                        403/400
5,549,612 A * 8/1996 Yapp .................. A61B 17/7059
                                                                        606/293

(Continued)

FOREIGN PATENT DOCUMENTS

JP    2001525213 A    12/2001
JP    2011500292 A    1/2011

OTHER PUBLICATIONS

International Search Report for PCT/IB2016/056769, dated Jan. 25, 2017, 2 pages.

(Continued)

*Primary Examiner* — Eduardo C Robert
*Assistant Examiner* — Michelle C Eckman
(74) *Attorney, Agent, or Firm* — Meunier Carlin & Curfman LLC

(57) ABSTRACT

An occipital plate for occipito-cervical fixation, comprising: a substantially flat plate provided with at least one fixation area connectable to the skull of a patient and at least one pair of through slots extending length-wise away from each other; and at least one pair of clamps slidably constrained each in a respective slot to move along a medial-lateral adjustment direction and provided with respective seats for receiving a support bar, wherein each receiving seat has an opening for insertion of the respective support bar accessible laterally and longitudinally along an insertion direction (Continued)

substantially parallel to a lying plane of the plate. Other aspects are disclosed and claimed.

10 Claims, 4 Drawing Sheets

(56) References Cited

U.S. PATENT DOCUMENTS

| | | | |
|---|---|---|---|
| 6,368,320 B1 | 4/2002 | Le Couedic et al. | |
| 9,381,044 B2* | 7/2016 | Robinson | A61B 17/7052 |
| 9,387,013 B1* | 7/2016 | Shoshtaev | A61B 17/7052 |
| 2002/0120268 A1* | 8/2002 | Berger | A61B 17/7055 606/300 |
| 2003/0153913 A1* | 8/2003 | Altarac | A61B 17/7044 606/278 |
| 2005/0240181 A1* | 10/2005 | Boomer | A61B 17/7041 606/914 |
| 2005/0240185 A1* | 10/2005 | Boomer | A61B 17/7055 606/277 |
| 2005/0283153 A1* | 12/2005 | Poyner | A61B 17/7044 606/53 |
| 2005/0288669 A1* | 12/2005 | Abdou | A61B 17/6433 606/246 |
| 2006/0155284 A1* | 7/2006 | Doherty | A61B 17/1615 606/86 B |
| 2006/0229610 A1* | 10/2006 | Piehl | A61B 17/7055 606/71 |
| 2007/0299441 A1 | 12/2007 | Hoffman et al. | |
| 2008/0051783 A1* | 2/2008 | Null | A61B 17/7055 606/261 |
| 2008/0086124 A1* | 4/2008 | Forton | A61B 17/7055 606/60 |
| 2008/0125781 A1* | 5/2008 | Hoffman | A61B 17/7055 606/331 |
| 2008/0147123 A1* | 6/2008 | Schermerhorn | A61B 17/7011 606/278 |
| 2008/0177313 A1* | 7/2008 | Lemoine | A61B 17/7055 606/250 |
| 2008/0177314 A1* | 7/2008 | Lemoine | A61B 17/7055 606/250 |
| 2009/0270924 A1* | 10/2009 | Wing | A61B 17/7011 606/280 |
| 2010/0094351 A1* | 4/2010 | Haggenmaker | A61B 17/7044 606/286 |
| 2010/0125299 A1* | 5/2010 | Paul | A61B 17/7044 606/280 |
| 2010/0211100 A1* | 8/2010 | Mack | A61B 17/7037 606/246 |
| 2010/0222825 A1 | 9/2010 | Paul et al. | |
| 2010/0324557 A1* | 12/2010 | Cheema | A61B 17/705 606/70 |
| 2011/0087288 A1 | 4/2011 | Stevenson et al. | |
| 2011/0087292 A1* | 4/2011 | Sandhu | A61B 17/7055 606/264 |
| 2011/0106085 A1* | 5/2011 | Null | A61B 17/7055 606/70 |
| 2011/0190824 A1* | 8/2011 | Gephart | A61B 17/70 606/278 |
| 2012/0035659 A1 | 2/2012 | Barrus et al. | |
| 2012/0065686 A1* | 3/2012 | Black | A61B 17/7055 606/252 |
| 2012/0078306 A1* | 3/2012 | Lynch | A61B 17/705 606/264 |
| 2013/0023939 A1* | 1/2013 | Pischl | A61B 17/8047 606/286 |
| 2013/0096614 A1 | 4/2013 | Zhang | |
| 2013/0172936 A1* | 7/2013 | Berrevoets | A61B 17/7055 606/278 |
| 2013/0238033 A1* | 9/2013 | Black | A61B 17/7055 606/286 |
| 2014/0088649 A1* | 3/2014 | Refai | A61B 17/7013 606/256 |
| 2014/0200613 A1* | 7/2014 | Dirisio | A61B 17/7059 606/246 |
| 2014/0214083 A1* | 7/2014 | Refai | A61B 17/7019 606/256 |
| 2014/0228891 A1* | 8/2014 | Hammer | A61B 17/7055 606/278 |
| 2014/0257400 A1 | 9/2014 | George et al. | |
| 2014/0324108 A1* | 10/2014 | Orbay | A61B 17/8052 606/289 |
| 2019/0117274 A1* | 4/2019 | Purcell | A61B 17/7055 |

OTHER PUBLICATIONS

Japanese Office Action for Application No. 2018-525707, dated Sep. 13, 2019, 6 pages.
English Translation of Notice of Reasons for Refusal issued in JP 2018-525707, dated Jan. 8, 2020, 14 pages.

* cited by examiner

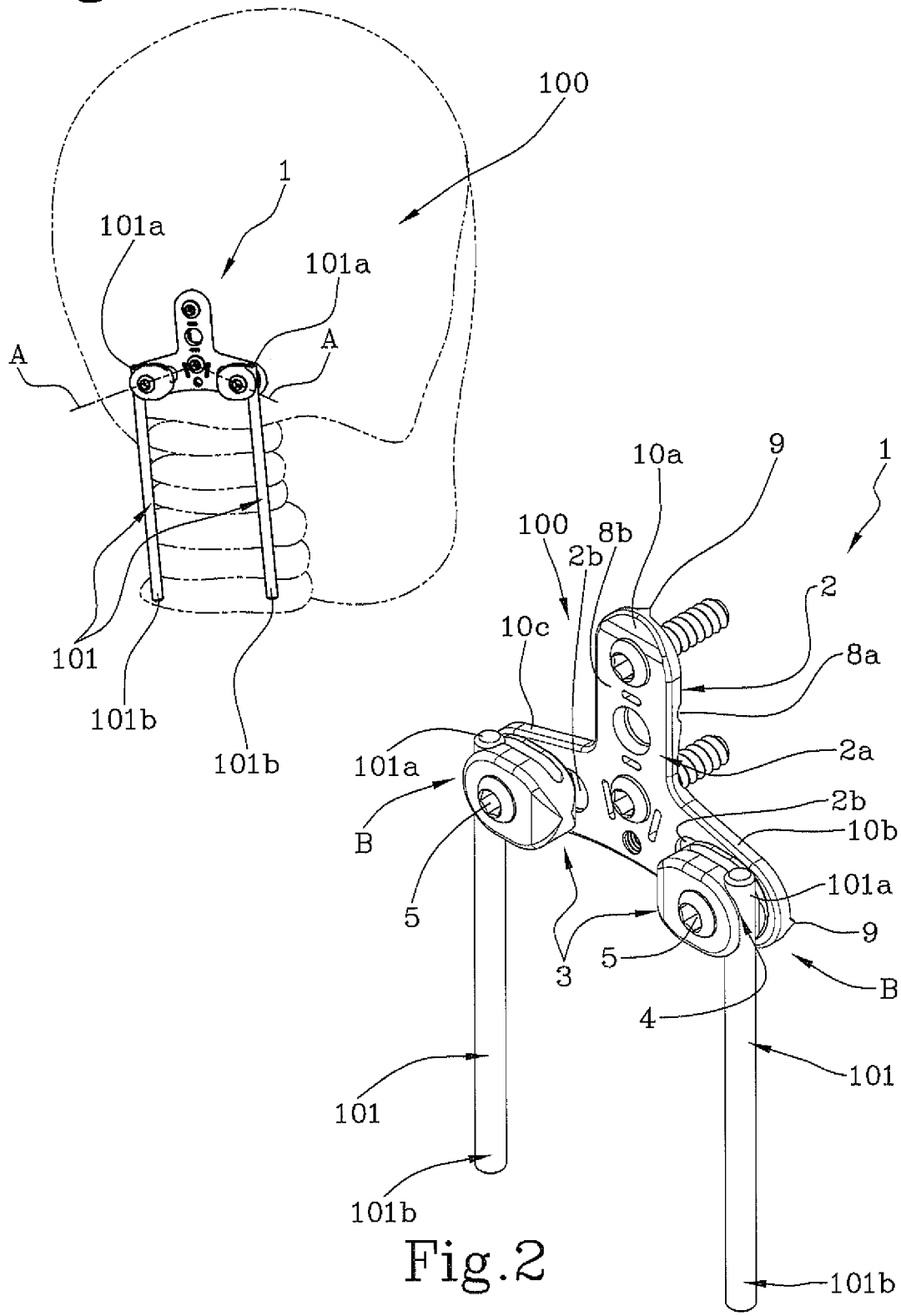

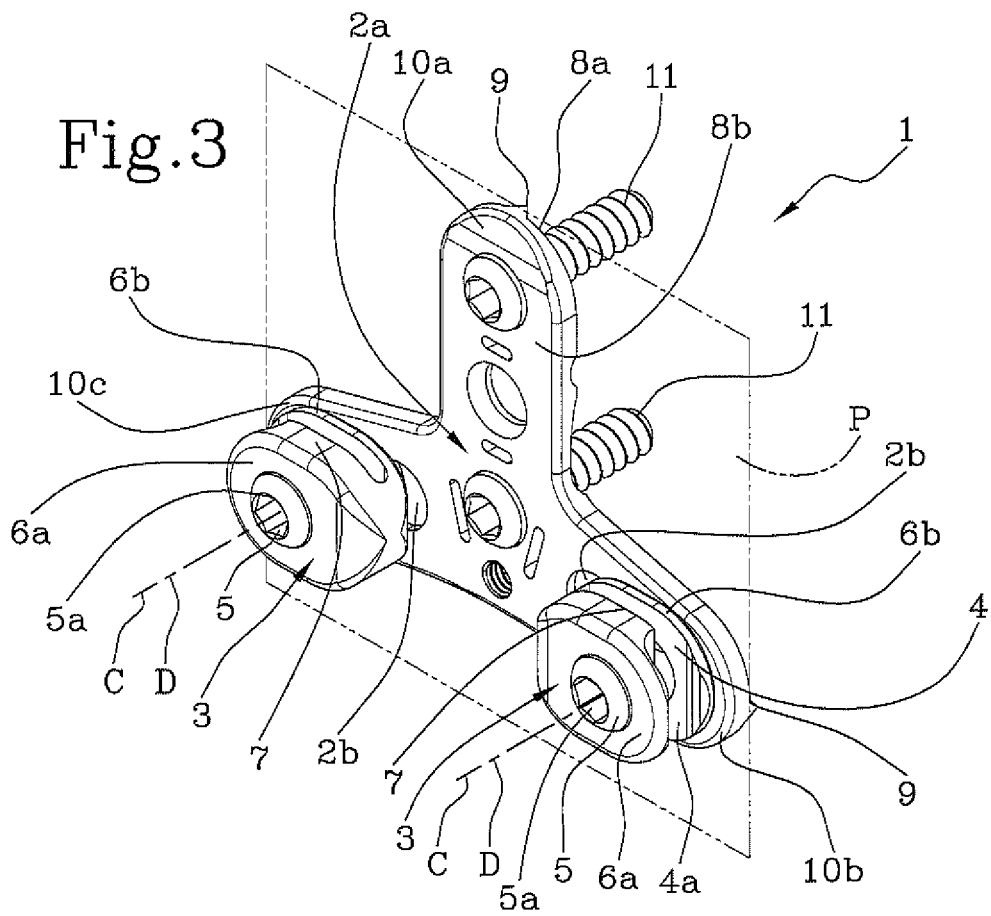
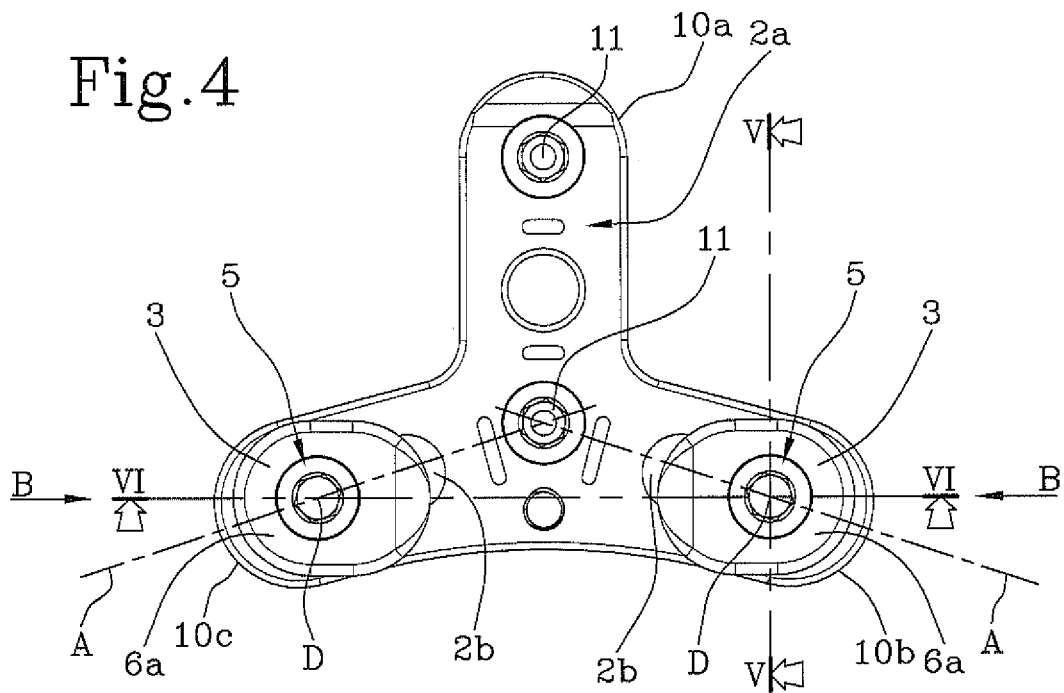

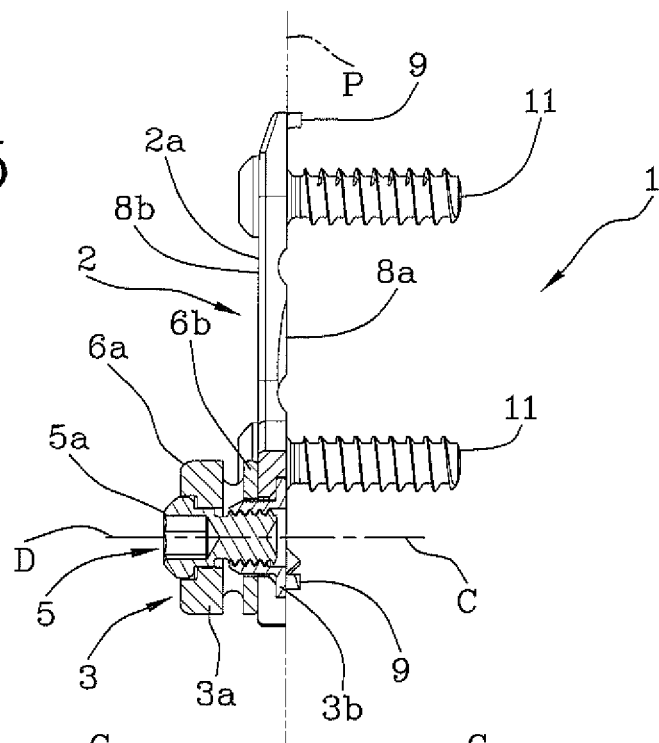
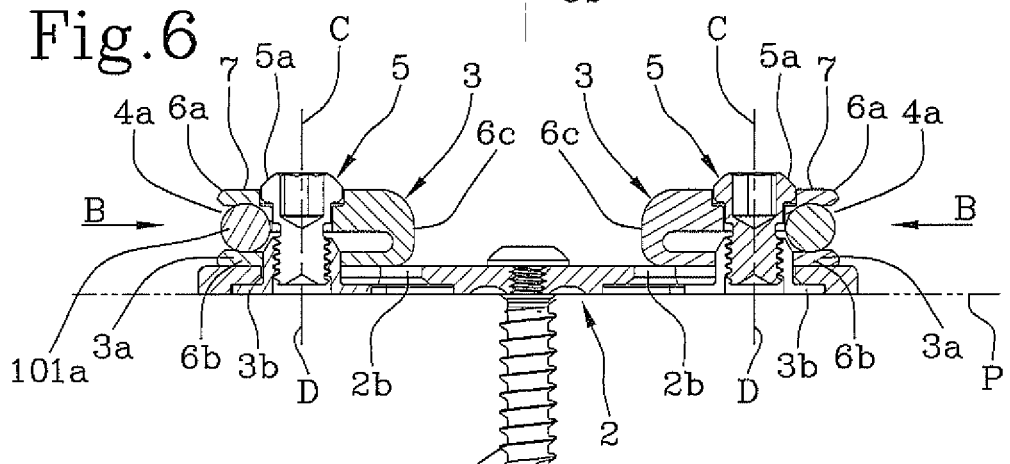
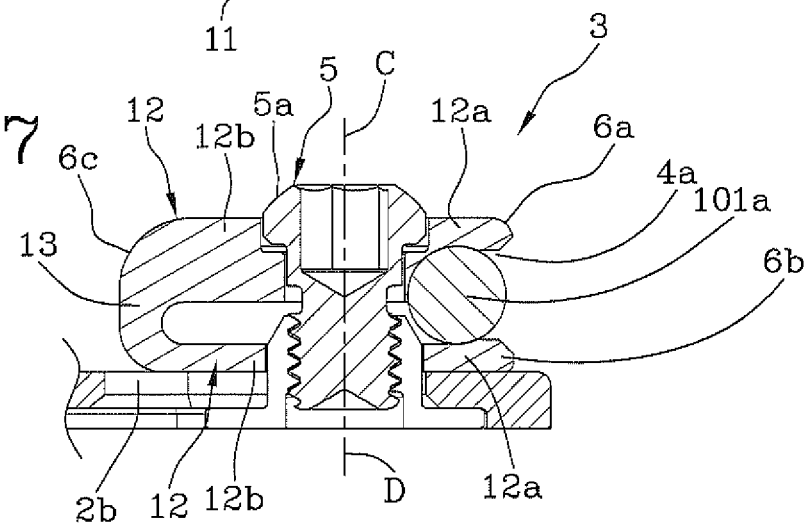

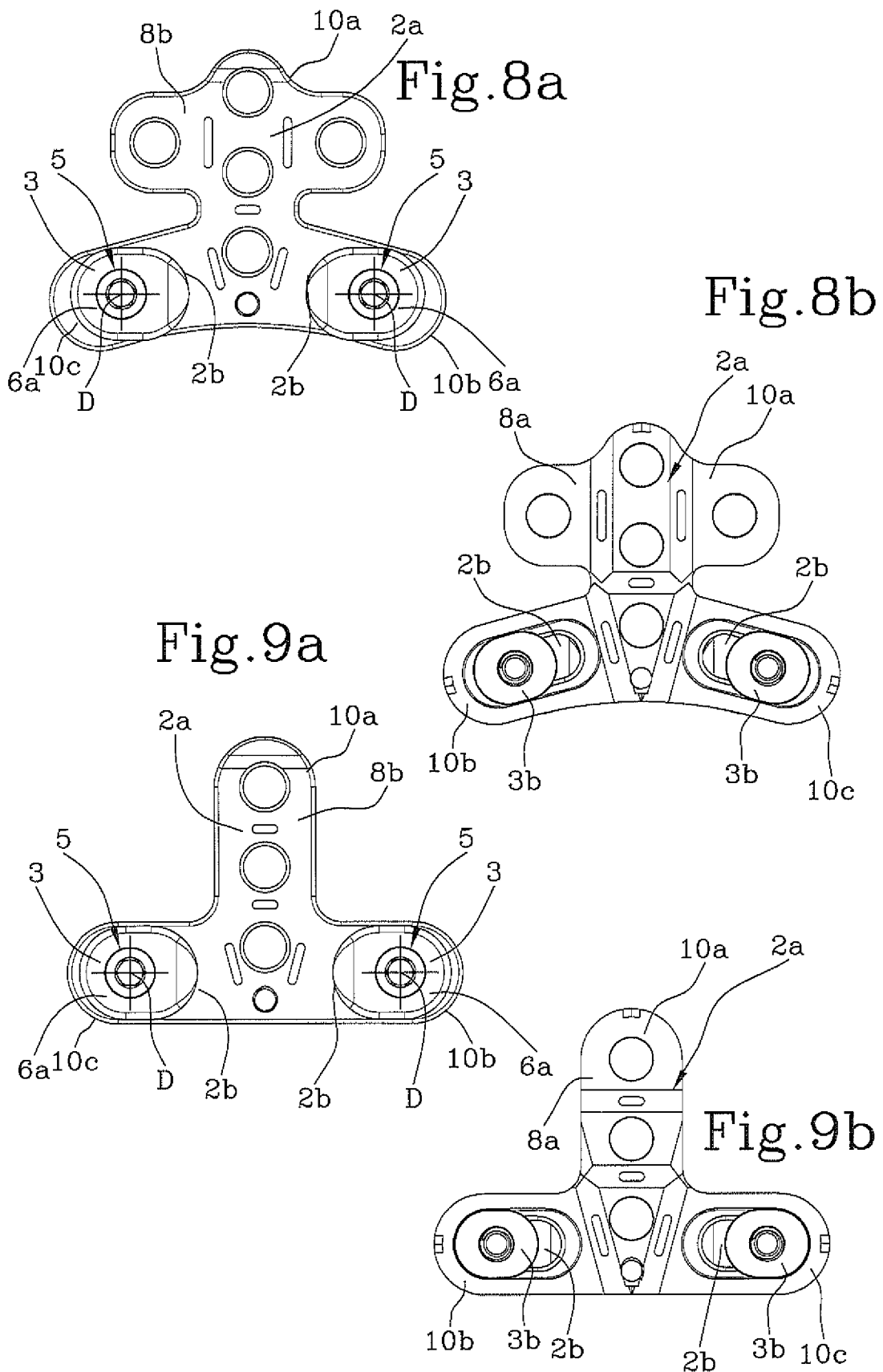

OCCIPITAL PLATE FOR OCCIPITO-CERVICAL FIXATION AND SYSTEM FOR OCCIPITO-CERVICAL FIXATION

The present application is a National Phase Entry of PCT International Application No. PCT/IB2016/056769 which was filed on Nov. 10, 2016, and which claims priority to Application No. 102015000074797 filed in Italy on Nov. 20, 2015, the contents of which are hereby incorporated by reference.

The present invention refers to an occipital plate for occipito-cervical fixation and a system for occipito-cervical fixation Therefore, the present invention finds particular application in the biomedical field and, especially, in the manufacturing of fixation systems for spinal surgery.

As known, the fixation devices are used in orthopaedic surgery to stabilize bones such as those of the vertebral column, providing support in the event of damage to the vertebral column.

One type of fixation device comprises a plate associable to a portion of a bone, either directly or through other connecting devices. For example, the posterior fixation devices may include a plate fixed to the skull, or an occipital plate, one or more longitudinal bars extending along the vertebral column and connected to the plate and a series of components for fixation to the bar, such as cables, wires, hooks, screws or other connectors attached to a vertebra.

Until a few years ago, it was possible to connect the fixation system only by achieving a perfect alignment between the various elements, for which reason the anatomy of each patient, which is different for each individual, needed to provide a wide range of components to be selected and assembled case-by-case, with a considerable cost of assembly and "delivery" that had to be paid by the facility performing the surgery.

Moreover, the need for a perfect alignment and positioning of the bars with respect to the occipital plate often required a direct intervention by the surgeon (or the staff) for dimensional and shape adjustments to be made to the components, which had a non negligible impact on both the surgery quality and time.

In order to prevent such a problem from occurring, over the years solutions have been developed to better meet the speed and precision requirements of the surgeon, such as the solution shown in the document U.S. Pat. No. 8,147,527, where the fixation system involves the use of a three-lobes occipital plate in order to accommodate the different size and anatomy of each patient, each of the side lobes is provided with a through slot inside which a clamp for receiving the longitudinal bar can slide.

Similar plates or devices are known in the document U.S. Pat. No. 8,894,695, in which the precision adjustment of the medial-lateral position of the bar is again achieved by having the clamp sliding in the through slot.

Obviously, these plates while facilitating the work of the surgeon if compared to what it was necessary in the past, however, do not provide a solution to the main problem related to these surgeries, i.e. the invasiveness of the components.

In fact, all known plates to date have a bar-plate coupling system defined by a base body that is slidably inserted in the through slot and provided with a central groove, accessible from above, in which the bar is removably insertable.

To allow the coupling between the bar and the base body, i.e. to fix the relative position and prevent it from decoupling, a "screw" clamping body is also provided, which is insertable in the groove, again from above, and screwable orthogonally respect to the bar in so as to be positioned against a side thereof pressing it against the base of the groove.

Therefore, it is clear is that the known systems need a plurality of components "stacked" on each other on the top of the plate and thus creating a non-negligible thickness, particularly considering the application area of the plate. Moreover, the (technical) need of a having lasting and strong tightening system implies the realization of a clamping body having a high number of threads, and therefore being substantially long.

In addition, note that, regardless of its size, a fixation system such as the one above described, is characterized by poor precision.

In fact, between the placement of the bar inside the groove and its locking, what is necessary is to position and tighten a further component without having the real possibility of constrain the bar and the base body, even on a temporary basis.

Therefore, object of the present invention is to provide an occipital plate for occipito-cervical fixation and a system for occipito-cervical fixation able to overcome the above mentioned problems related to the know technique.

More precisely, object of the present invention is to provide an occipital plate for occipito-cervical fixation easy to adjust and having a small size.

Moreover, object of the present invention is provide a system for occipito-cervical fixation easy to be positioned and adjusted.

Such objects are achieved by an occipital plate for occipito-cervical fixation, as well as by a system for occipito-cervical fixation.

In particular, the occipital plate for occipito-cervical fixation comprising a substantially flat plate provided with at least one fixation area connectable to the skull of a patient and at least one pair of through slots extending length-wise away from each other; at least one pair of clamps slidably constrained each in a respective slot to move along a medial-lateral adjustment direction and provided with respective seats for receiving a support bar.

According to one aspect of this invention, each receiving seat has an insertion opening for a laterally and/or longitudinally accessible support bar along an insertion direction that is substantially parallel to the development plan of said plate.

Advantageously, thanks to the possibility of carrying out a lateral insertion, the clamp thickness is dramatically reduced, even in light of the fact that the clamp tightening elements may be placed at the same level as the level of the bar receiving seat.

However, these and other features, as well as their technical advantages, will become more apparent from the following illustrative, and therefore not limitative, description of a preferred, and therefore not exclusive, embodiment of an occipital plate and occipito-cervical fixation system as shown in the following attached figures, where:

FIG. 1 shows a perspective view of an occipito-cervical fixation system according to the present invention in a condition of use;

FIG. 2 shows the system illustrated in FIG. 1 when not in use;

FIG. 3 shows a perspective view of an occipital plate for occipito-cervical fixation according to the present invention;

FIG. 4 shows a plan view of the plate shown in FIG. 3;

FIG. 5 shows a section view of the plate according to the V-V section line shown in FIG. 4;

FIG. 6 shows a section view of the plate according to the VI-VI section line shown in FIG. 4;

FIG. 7 shows a detail of FIG. 6

FIGS. 8a, 8b show views from above and below of an occipital plate according to the present invention in a second embodiment;

FIGS. 9a, 9b show views from above and below of an occipital plate according to the present invention in a third embodiment;

With reference to the attached figures, number 1 refers to an occipital plate for occipito-cervical fixation according to the present invention.

This plate 1 is therefore especially used in spinal surgery, mainly to firmly connect to the occipital area (i.e. the skull) of the patient and the cervical vertebrae in order to create a stable support for the head.

This plate 1 is therefore used within a system 100 or an occipito-cervical fixation system, which defines the connection element with the occipital portion, i.e. the skull.

The remaining components of the system 100 are preferably defined by at least one longitudinal support bar 101, more preferably at least two, each extending between a first end portion 101a fixed to the plate 1 and a second end portion 101b fixed/fixable to a vertebra.

In certain embodiments, a crosspiece (not shown in the Figure) is also envisaged which is connected or connectable to the vertebrae.

When in use, the longitudinal bars 101 can (must) be bent according to the patient's physiognomy.

In this respect, preferably, the crosspiece is fixed or fixable to the vertebrae by screws, preferably polyaxial screws, to which the second end portions 101b of the bars 101 are also connected, or it is fixed with clamps directly on the longitudinal bars 101.

As far as the polyaxial screws, see what is described and illustrated in pages 8 to 11 of the patent application MI2014A001383 of the Applicant. Each first end portion 101a of bar 101 is instead fixed to the plate 1 by means of a special clamp 3.

More precisely, the plate 1 comprises a substantially flat plate 2 extending substantially in its own lying plane "P", which when in use can be bent to fit the plate to the patient's cranial shape.

In this respect, the plate 2 has a plurality of weakening grooves for defining the direction of bending/curvature.

This plate 2 is provided with at least one fixing zone 2a, connected to the skull of a patient, and at least a pair of through slots 2b extending length-wise away from each other along respective medium-side adjustment directions "A".

Thus, the through slots 2b develop between the respective first ends proximal to each other, and second ends distal to each other.

The fixing area 2a is connected to the skull by means of suitable fastening elements 11, preferably screws.

In the illustrated embodiment, the plate 2 show three end portions 10a, 10b, 10c.

More precisely, a first end portion 10a shows at least said fixation area 2a and a second 10b and a third end portions 10c show each one through slot 2b.

In certain alternative embodiments, plate 2 can also have more than three end portions.

For example, in the embodiment of FIG. 8a, 8b, the plate has five end portions (five-lobed plate) and a greater number of fixation openings.

Furthermore, note that in certain embodiments, the end portions are substantially angularly equally spaced (FIGS. 1-7), but in other embodiments (FIGS. 8a, 8b, 9a, 9b), they can be arranged according to another orientation, such as an inverted "T" conformation.

In other words, in the embodiment of FIG. 9a, 9b, the second and the third end portions are aligned with each other.

Note that plate 2 has a first internal face 8a in use, and a second external face 8b in use, opposing each other.

When in use, the first face 8a of the plate 2 is positioned on to the patient's skull, while the second face 8b is facing away from it.

In order to allow the firm positioning of the plate 1 onto the patient's skull, even upon inserting the plate, the first face 8a has a plurality of gripping teeth 9, or claws, extending away from the second face 8b and shaped to penetrate into the patient's skull.

These gripping teeth 9 are arranged along the peripheral portion of the first face 8a in order to impart stability to the positioning, minimizing the possibility of rotations in the lying plane "P".

Preferably, the teeth 9 are triangularly shaped, protruding from the first face 8a of the plate for a limited development in order to grip on the skull without damaging it.

Furthermore, the plate 1 has at least a pair of said clamps 3, each one slidably connected to the respective through slot 2b to move along their respective direction of medial-lateral adjustment "A".

Therefore, the clamps 3 have a grip portion 3a and a carriage 3b slidably constrained to the through slot 2b.

Preferably, the clamps 3 protrude from the second face 8b away from the plate 2.

Each one of these clamps 3 (at the grip portion 3a) is provided with at least a corresponding receiving seat 4 of a support bar 101 (in particular at least of one end portion 101a thereof).

More precisely, each receiving seat 4 has an access point 4a for a support bar 101 that is laterally and/or longitudinally accessible along an insertion direction "B" that is substantially parallel to the lying plane "P" of the plate 2.

In other words, the access point 4a (or opening) of the seat 4 has a orientation tangential to the lying plane "P", i.e. to the plate 2.

In addition, preferably, the receiving seats 4 of the clamps 3 have an elongated shape for housing a portion (the end portion 101a) of the respective support bar 101.

Indeed, preferably, the insertion direction "B" is parallel to the lying plane "P" and orthogonal to the development direction of the bar 101.

Advantageously, thanks to the possibility of carrying out a lateral insertion, the clamp thickness is dramatically reduced, even in light of the fact that the clamp tightening elements may be placed at the same level as the level of the bar receiving seat.

In this regard, each clamp 3 comprises a clamping member 5 associated with the receiving seat 4 and configured to lock the position of the bar 101 in the seat 4.

In the preferred embodiment, the clamping member 5 has an operational direction "C" that is substantially orthogonal to said insertion direction "B". Therefore, preferably, the operational direction "C" of the clamping member 5 is orthogonal to the lying plane "A" of the plate 2.

In other words, the operational direction "C" is transverse, or orthogonal, to the insertion direction "B".

The clamping member 5 is preferably of a screw type element, coupleable to said access point 4a of seat 4 so to tighten it.

Therefore, the clamping member is accessible to the operator orthogonally to the plate 2 (from an upper area).

In order to minimize the thickness of plate 1, the clamping member 5 and the seat 4 are preferably arranged side by side, i.e. at least partially positioned at the same distance (or level) from the lying plane "P".

In this respect, the receiving seat 4 is preferably delimited by at least a first 6a and a second 6b jaws, facing each other and spaced apart to define the access point 4a.

The first clamp 6a is distally positioned in respect to plate 2 (i.e. the lying plane "P") if compared to the second clamp 6b.

Therefore, the first clamp 6a and the second clamp 6b have end portions defining the seat 4.

More precisely, these end portions are bent to define the housing of the bar 101.

The clamping member 5 (i.e. the clamping screw 5a) is thus operatively active transversely to the plate 2 to move the first clamp 6a approaching the second clamp 6b, or vice versa, in order to tighten the receiving seat 4. Preferably, the clamping member 5 is active on the jaws 6a, 6b at an area next to the end portion.

Therefore, the jaws 6a, 6b have a movement portion 6c next to the end portions 6a, 6b and associated to the clamping member 5 (i.e. the screw 5a).

In detail, each clamp 3 is defined by two discs 12 facing each other and spaced apart, connected by an elastic connection 13.

Said discs 12 have respective first half-parts 12a facing each other and defining the receiving seat 4 and respective second half-parts 12b facing each other and having coaxial openings for receiving the clamping member 5.

Preferably, the receiving seats 4 of the clamps 3 have elastic restraining devices 7 configured to keep the bar 101 inside the seat 4 after it has been inserted.

More preferably, such retaining devices 7 are defined by the elastic deformability of the jaws 6a, 6b.

In order to allow an even more agile and precise adjustment of the fixation system 100, the clamps 3 are rotatably coupled to each through slot 2b of the plate so as to rotate about the respective axis "D" that is orthogonal to the lying plane "P" of the plate 2.

This axis "D" is orthogonal to the insertion direction "B".

Therefore, each grip portion 3a of the clamp 3 is preferably pivotally coupled (i.e. overlapped) to the respective carriage 3b.

Advantageously, in such a way, it is possible to adapt the orientation of the clamp in relation to the bar 101 both before and, if appropriate, after the coupling of the bar 101 with the seat 4, while giving the maximum agility and versatility to the surgeons.

Note that the clamping member 5 is preferably coupled with the carriage 3b in such a way that, when in the locking position, said carriage 3b is connected to the plate 2.

The invention achieves the intended objects and achieves important advantages.

In fact, the presence of a plate having medial-laterally sliding clamps that are laterally accessible, guarantees the maximum level of application versatility to the surgeon while limiting the overall dimensions.

Furthermore, the presence of the gripping teeth allows a safe and firm positioning, even insertion.

Still, the possibility of rotating around its own axis, together with the medial-lateral sliding movement, maximizes the possibility and easiness of adjustment of the clamp position and the bar orientation.

The invention claimed is:

1. An occipital plate for occipito-cervical fixation, comprising:
    a substantially flat plate provided with at least one fixation area connectable to the skull of a patient and at least one pair of through slots set a distance from the fixation area extending length-wise away from each other; and
    at least one pair of clamps, wherein each clamp of said pair of clamps is slidably constrained in a respective through slot to move along a medial-lateral adjustment direction and provided with respective receiving seats for receiving a support bar, wherein each receiving seat has an insertion opening for insertion of the respective support bar accessible laterally and longitudinally along respective insertion directions substantially parallel to a lying plane of the substantially flat plate;
    wherein the receiving seat of each clamp of said pair of clamps has an elastic retaining means configured to provisionally keep the respective support bar inside the receiving seat once inserted;
    wherein each clamp of said pair of clamps comprises a clamping member associated with the receiving seat and configured to lock the position of the respective support bar in the receiving seat;
    wherein each clamp of said pair of clamps is also rotatably coupled to the respective through slot so as to rotate about a respective axis perpendicular to the lying plane of the substantially flat plate and set at a distance from the fixation area.

2. The occipital plate according to claim 1, wherein the insertion opening of each receiving seat is oriented tangentially to the substantially flat plate.

3. The occipital plate according to claim 1, wherein:
    each receiving seat has at least a first and a second jaw facing each other and spaced apart to define the insertion opening, in which the first jaw is distal from the substantially flat plate with respect to the second jaw; and
    the clamping member is operatively active transversely to the substantially flat plate for moving the first jaw closer to the second jaw, or vice versa, in order to tighten the receiving seat.

4. The occipital plate according to claim 3, wherein the clamping member comprises a screw coupled with a body of the respective clamp and extending orthogonally to the lying plane of the substantially flat plate.

5. The occipital plate according to claim 3, wherein the receiving seats for each clamp of said pair of clamps has an elongated conformation to house a portion of the respective support bar.

6. The occipital plate according to claim 1, wherein:
    the substantially flat plate has a first face, in use on the inside, and a second face, in use on the outside, opposing each other, wherein each clamp of said pair of clamps protrudes from the second face away from the substantially flat plate;
    the first face having a plurality of gripping teeth, or claws, extending away from the second face.

7. The occipital plate according to claim 6, wherein the gripping teeth are arranged along a periphery of the first face.

8. The occipital plate according to claim 1, wherein the substantially flat plate has three end portions, in which:
    a first end portion has at least the fixation area;

a second and a third end portion have respectively a through slot each.

9. A system for occipito-cervical fixation, comprising:

a substantially flat plate provided with at least one fixation area connectable to the skull of a patient and at least one pair of through slots set at a distance from the fixation area and extending length-wise away from each other;

at least one pair of clamps, wherein each clamp of the pair of claims is slidably constrained in a respective through slot to move along a medial-lateral adjustment direction and provided with respective receiving seats for receiving a support bar, wherein each receiving seat has an insertion opening for insertion of the respective support bar accessible laterally and longitudinally along respective insertion directions substantially parallel to a lying plane of the substantially flat plate;

at least two joining screws inserted in the fixation area and perpendicular to said lying plane of the substantially flat plate for connection to the skull of a patient;

a pair of longitudinal support bars, each having an end portion inserted in a corresponding receiving seat of a clamp of the pair of clamps;

wherein the receiving seat of each clamp of the pair of clamps has an elastic retaining means configured to provisionally keep the respective support bar inside the receiving seat once inserted;

wherein each clamp of the pair of clamps comprises a clamping member associated with the receiving seat and configured to lock the position of the respective support bar in receiving the seat;

wherein each clamp of the pair of clamps is also rotatably coupled to the respective through slot so as to rotate about a respective axis parallel the at least two joining screws.

10. The system for occipito-cervical fixation according to claim 9, wherein the at least two joining screws are polyaxial.

* * * * *